(12) United States Patent
Kim et al.

(10) Patent No.: US 8,801,616 B2
(45) Date of Patent: Aug. 12, 2014

(54) ULTRASONIC DIAGNOSTIC APPARATUS AND ULTRASONIC IMAGE PROCESSING METHOD

(75) Inventors: Gyu Won Kim, Gyunggi-do (KR); Won Tae Choi, Gyunggi-do (KR); Kyoung Joong Min, Seoul (KR)

(73) Assignee: Samsung Electro-Mechanics Co., Ltd., Gyunggi-Do (KR)

( * ) Notice: Subject to any disclaimer, the term of this patent is extended or adjusted under 35 U.S.C. 154(b) by 435 days.

(21) Appl. No.: 12/753,724

(22) Filed: Apr. 2, 2010

(65) Prior Publication Data

US 2011/0190632 A1    Aug. 4, 2011

(30) Foreign Application Priority Data

Jan. 29, 2010   (KR) .................. 10-2010-0008529

(51) Int. Cl.
*A61B 8/00*    (2006.01)

(52) U.S. Cl.
USPC ............ 600/443; 600/453; 600/458; 382/128

(58) Field of Classification Search
USPC .................................. 600/458, 443
See application file for complete search history.

(56) References Cited

U.S. PATENT DOCUMENTS

| | | | | |
|---|---|---|---|---|
| 5,123,417 | A | * | 6/1992 | Walker et al. ............ 600/455 |
| 5,638,820 | A | * | 6/1997 | Chen et al. ............... 600/437 |
| 7,333,543 | B2 | * | 2/2008 | Choi ..................... 375/240.16 |
| 2004/0081340 | A1 | * | 4/2004 | Hashimoto ............... 382/128 |
| 2008/0242999 | A1 | * | 10/2008 | Kakee ..................... 600/458 |

* cited by examiner

*Primary Examiner* — Tse Chen
*Assistant Examiner* — Patricia Park
(74) *Attorney, Agent, or Firm* — Bracewell & Giuliani LLP; Brad Y. Chin

(57) ABSTRACT

Disclosed herein is an ultrasonic diagnostic apparatus and ultrasonic image processing method. The ultrasonic diagnostic apparatus includes an ultrasonic transmission unit; An ultrasonic probe emits; An ultrasonic reception unit; An image processing unit; A sound velocity determination unit; and A control unit. Accordingly, there is an advantage in that the actual sound velocity of a reflected wave is estimated, so that high-quality ultrasonic images can be provided, and the time required for the estimation of a sound velocity can be reduced.

4 Claims, 5 Drawing Sheets

FIRST FRAME

SECOND FRAME n-TH FRAME
(20-TH FRAME)

ULTRASONIC DIAGNOSTIC APPARATUS AND ULTRASONIC IMAGE PROCESSING METHOD

CROSS REFERENCE TO RELATED APPLICATION

This application claims the benefit of Korean Patent Application No. 10-2010-0008529, filed on Jan. 29, 2010, entitled "Ultrasonic Diagnosis Apparatus and Method for Processing Ultrasonic Image", which is hereby incorporated by reference in its entirety into this application.

BACKGROUND OF THE INVENTION

1. Technical Field

The present invention relates generally to an ultrasonic diagnostic apparatus and ultrasonic image processing method.

2. Description of the Related Art

An ultrasonic diagnostic apparatus is one of the important diagnostic apparatuses that have been variously applied. In particular, ultrasonic diagnostic apparatuses have been widely used in the medical field thanks to the characteristics of being non-invasive and non-destructive to a target. Recent high-performance ultrasonic systems are being used to generate a two-dimensional or three-dimensional image of the inside of a target.

Generally, an ultrasonic diagnostic apparatus is configured to receive the echoes which are obtained when a part of the ultrasonic waves transmitted from an ultrasonic probe are reflected from a structural variation point (variation plane) of the internal tissue of the target, and to generate a tomogram of the target on the basis of the echoes.

In this way, an ultrasonic image is generated by collecting reflected waves (echoes) which are returned from the internal tissue of the target while ultrasonic waves emitted from the ultrasonic probe are propagated to the internal tissue of the target.

In order to diagnose the internal tissue of a human body, conventional ultrasonic diagnostic apparatuses are operated to generate an ultrasonic image, as described above. In this case, a beam is focused on the assumption that all the regions of the internal tissue of a human body have the same sound velocity (for example, about 1540 m/s). However, the tissue of a human body has a unique sound velocity depending on the type of media.

Therefore, a difference may occur between the actual sound velocity and the assumed sound velocity for each tissue of a human body, and may influence reflected waves which are returned from each tissue of the human body after the ultrasonic beam has been reflected from the tissue.

Accordingly, as the difference between the actual sound velocity and the assumed sound velocity of each internal tissue of the human body increases, a difference between the reflected waves may also increase. As a result, a problem arises in that the beam reflected from the internal tissue of the human body is defocused, so that an image is distorted, thus deteriorating resolution and tissue contrast.

SUMMARY OF THE INVENTION

Accordingly, the present invention has been made keeping in mind the above problems occurring in the prior art, and the present invention is intended to provide an ultrasonic diagnostic apparatus and ultrasonic image processing method, which estimates the actual sound velocities corresponding to various internal tissues of a human body, and applies the estimated actual sound velocities to the ultrasonic diagnostic apparatus, thus improving the resolution and tissue contrast of clinical ultrasonic images.

Further, the present invention is intended to provide an ultrasonic diagnostic apparatus and ultrasonic image processing method, which compares only part of ultrasonic images rather than all of them, thus decreasing the time required for the estimation of the actual sound velocity.

In accordance with an aspect of the present invention, there is provided an ultrasonic diagnostic apparatus, comprising an ultrasonic transmission unit for generating a transmission signal in response to a control signal and converting the transmission signal into an ultrasonic beam; an ultrasonic probe for emitting the ultrasonic beam to a target and receiving a reflected wave which is returned from the target; an ultrasonic reception unit for generating a reception signal by converting the reflected wave into an electrical signal; an image processing unit for generating primary ultrasonic image data of a plurality of frames by dividing the reception signal into a plurality of signals, each with a predetermined sound velocity, and also generating secondary ultrasonic image data by extracting a contour from primary ultrasonic image data of an optimal frame of the plurality of frames; a sound velocity determination unit for dividing primary ultrasonic image data of any one frame among primary ultrasonic image data of the plurality of frames into a plurality of blocks, extracting block image data from individual blocks, selecting an optimal block from among the blocks, determining blocks at locations of remaining frames corresponding to a location of the optimal block to be optimal blocks of corresponding frames, extracting optimal block image data from respective optimal blocks of the frames, selecting an optimal frame from among the frames, and determining a sound velocity of the optimal frame to be an actual sound velocity of the reflected wave; and a control unit for generating the control signal and performing control such that the ultrasonic beam is generated in response to the control signal and the primary ultrasonic image data is generated by receiving the reflected wave of the ultrasonic beam, and such that the secondary ultrasonic image data is generated by determining the optimal sound velocity based on the primary ultrasonic image data.

In an embodiment, the ultrasonic diagnostic apparatus further comprises a data output unit for outputting the secondary ultrasonic image data.

In an embodiment, the image processing unit comprises an image extraction module for dividing the reception signal into the plurality of signals, each with a predetermined sound velocity, and extracting a plurality of image signals; and an image generation module for generating the primary ultrasonic image data of the plurality of frames based on the plurality of image signals, and generating the secondary ultrasonic image data by extracting the contour from primary ultrasonic image data of the optimal frame among the frames.

In an embodiment, the sound velocity determination unit comprises an image division module for dividing the primary ultrasonic image data of each of the frames into an equal number of blocks; a contour extraction module for generating a plurality of pieces of block image data by extracting contours from primary ultrasonic image data of individual blocks of any one of the frames, and also generating a plurality of pieces of optimal block image data by extracting contours from primary ultrasonic image data of respective optimal blocks of the frames; an image analysis module for calculating luminance values and High-Frequency (HF) component values of the plurality of pieces of block image data, and calculating luminance values and HF component values of the plurality of pieces of optimal block image data; an image comparison module for detecting a maximum luminance value and a maximum HF component value by individually comparing the luminance values and the HF component values of the plurality of pieces of block image data, and detecting a maximum luminance value and a maximum HF component value by individually comparing the luminance values and the HF component values of the plurality of pieces of optimal block image data; and a sound velocity determination module for selecting block image data having the maximum luminance value and the maximum HF component value from among the plurality of pieces of block image data and a block corresponding to the block image data as optimal block image data and an optimal block, respectively, determining blocks at locations of remaining frames corresponding to a location of the optimal block to be optimal blocks of corresponding frames, selecting a frame having the maximum luminance value and the maximum HF component value among the plurality of pieces of optimal block image data as an optimal frame, and determining a sound velocity of the optimal frame to be an optimal sound velocity of the reflected wave.

In an embodiment, the control signal is a signal required to perform control such that a transmission signal with a plurality of preset sound velocities is generated.

In an embodiment, the control signal is a signal required to perform control such that a transmission signal with the optimal sound velocity is generated.

In accordance with another aspect of the present invention, there is provided an ultrasonic image processing method, comprising (A) generating a transmission signal in response to a control signal, converting the transmission signal into an ultrasonic beam, and emitting the ultrasonic beam to a target; (B) receiving a reflected wave which is returned from the target after the ultrasonic beam has been reflected from the target, dividing the reflected wave into a plurality of reception signals, extracting the reception signals, generating primary ultrasonic image data of a plurality of frames from the reception signals, and storing the primary ultrasonic image data of the frames; (C) selecting an optimal block from any one frame of the primary ultrasonic image data of the plurality of frames, determining blocks at locations of remaining frames, corresponding to a location of the optimal block, to be optimal blocks of corresponding frames, selecting an optimal frame, and determining a sound velocity of the optimal frame to be an actual sound velocity of the reflected wave; and (D) generating secondary ultrasonic image data by extracting a contour from primary ultrasonic image data of the optimal frame, and then outputting the secondary ultrasonic image data.

In an embodiment, (C) comprises (C-1) reading the primary ultrasonic image data of the plurality of frames and dividing primary ultrasonic image data of each frame into a plurality of blocks; (C-2) generating a plurality of pieces of block image data by extracting contours from individual blocks of the primary ultrasonic image data of any one frame among the primary ultrasonic image data of the frames, and selecting an optimal block from the plurality of pieces of block image data; (C-3) determining blocks at locations of remaining frames, corresponding to the location of the optimal block, to be the optimal blocks of the corresponding frames, generating a plurality of pieces of optimal block image data by extracting contours from primary ultrasonic image data of the respective optimal blocks of the frames, and selecting the optimal frame from the plurality of pieces of optimal block image data; and (C-4) determining a sound velocity of the optimal frame to be an optimal sound velocity of the reflected wave.

In an embodiment, (C-2) comprises extracting the contours by performing a morphological operation on the primary ultrasonic image data of the plurality of blocks, thus generating the plurality of pieces of block image data; calculating luminance values and High-Frequency (HF) component values of the plurality of pieces of block image data; and individually comparing the luminance values and the HF component values, and selecting a block having a maximum luminance value and a maximum HF component value as the optimal block.

In an embodiment, (C-3) comprises determining the blocks at the locations of the remaining frames, corresponding to the location of the optimal block, to be the optimal blocks of the corresponding frames, and extracting the contours from the primary ultrasonic image data of the respective optimal blocks of the frames by performing the morphological operation on the primary ultrasonic image data, thus generating the plurality of pieces of optimal block image data; determining whether generation of all of optimal block image data of the respective optimal blocks of the frames has been completed; calculating luminance values and HF component values of the plurality of pieces of optimal block image data; and selecting a frame having a maximum luminance value and a maximum HF component value as the optimal frame by individually comparing the luminance values and the HF component values from the plurality of pieces of optimal block image data.

DESCRIPTION OF THE PREFERRED EMBODIMENTS

Figure 1:
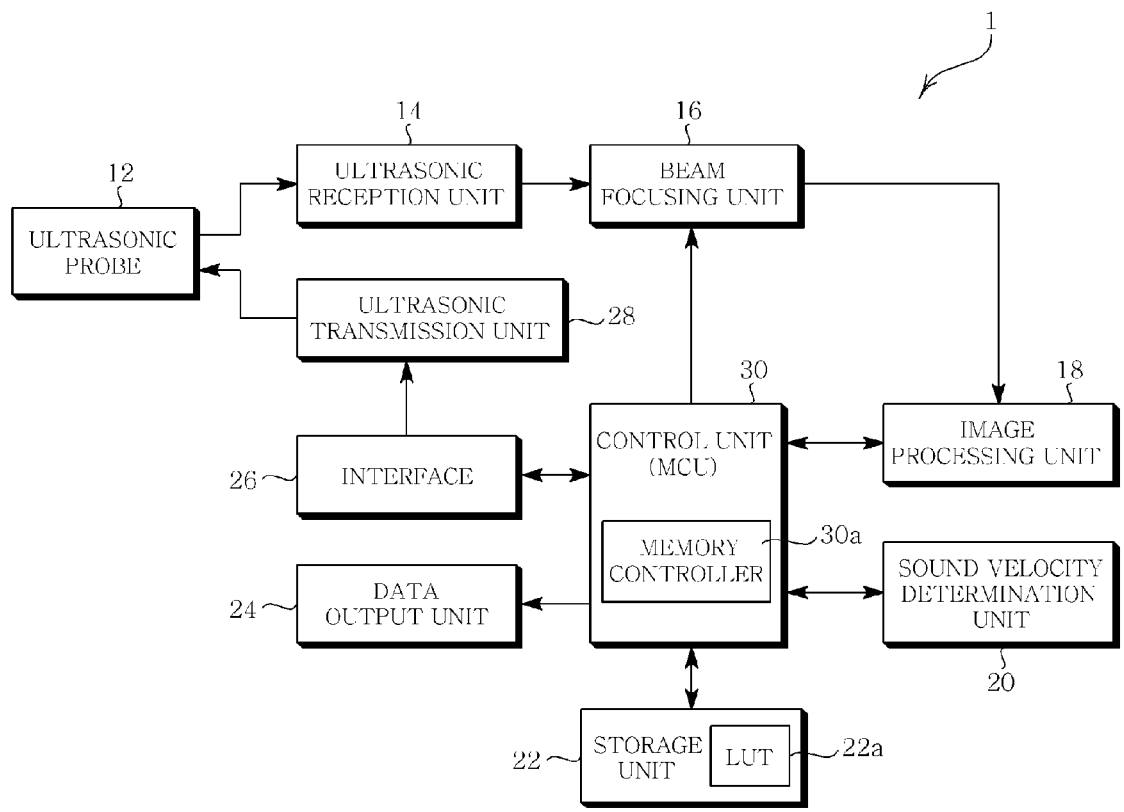
FIG. 1 is a block diagram showing an ultrasonic diagnostic apparatus according to an embodiment of the present invention.

Prior to giving the description, the terms and words used in the present specification and claims should not be interpreted as being limited to their typical meaning based on the dictionary definitions thereof, but should be interpreted to have the meaning and concept relevant to the technical spirit of the present invention on the basis of the principle by which the inventor can suitably define the implications of terms in the way which best describes the invention.

The above and other objects, features and advantages of the present invention will be more clearly understood from the following detailed description taken in conjunction with the accompanying drawings. In the present specification, reference now should be made to the drawings, in which the same reference numerals are used throughout the different drawings to designate the same or similar components. Further, in the description of the present invention, if detailed descriptions of related well-known constructions or functions are determined to make the gist of the present invention unclear, the detailed descriptions will be omitted.

Hereinafter, embodiments of the present invention will be described in detail with reference to the attached drawings.

FIG. 1 a block diagram showing an ultrasonic diagnostic apparatus according to an embodiment of the present invention.

Referring to FIG. 1, an ultrasonic diagnostic apparatus 1 according to an embodiment of the present invention includes an ultrasonic probe 12, an ultrasonic reception unit 14, a beam focusing unit 16, an image processing unit 18, a sound velocity determination unit 20, a storage unit 22, an interface 24, a data output unit 26, an ultrasonic transmission unit 28 and a control unit (microcontroller: MCU) 30.

The ultrasonic probe 12 emits an ultrasonic wave with a predetermined sound velocity into the body of an examinee, and receives an ultrasonic wave reflected from the internal tissue of the body of the examinee (hereinafter referred to as a 'reflected wave').

In detail, when the ultrasonic wave transmitted from the ultrasonic probe 12 comes into contact with the internal tissue of the body of the examinee, it is reflected, scattered or transmitted in correlation with various types of media of the tissue of the human body. The ultrasonic probe 12 receives a reflected wave which is returned from the internal tissue of the human body after the ultrasonic wave has been reflected therefrom.

In this way, in order to transmit or receive an ultrasonic wave to or from the body of the examinee through the ultrasonic probe 12, the ultrasonic transmission unit 28 for converting an ultrasonic wave into an electrical signal and the ultrasonic reception unit 14 for converting an electrical signal into an ultrasonic wave are required.

The ultrasonic transmission unit 28 generates an electrical signal (hereinafter referred to as a 'transmission signal') with a predetermined sound velocity in response to a control signal from the control unit 30, converts the transmission signal into an ultrasonic beam to be emitted into the body of the examinee, and transfers the ultrasonic beam to the ultrasonic probe 12.

The ultrasonic transmission unit 28 is configured to include a transmission beam former (not shown) for converting the transmission signal into an ultrasonic beam.

The transmitted signal is a signal with a sound velocity which is preset under the control of the control unit 30, or a signal with an optimal sound velocity which is determined by estimating the actual sound velocity of the reflected wave.

The ultrasonic reception unit 14 receives a reflected wave which is reflected from the internal tissue of the body of the examinee after the ultrasonic beam generated by the ultrasonic transmission unit 28 has been emitted into the body of the examinee through the ultrasonic probe 12, and transmits the reflected wave to the beam focusing unit 16.

The ultrasonic reception unit 14 is configured to include a reception beam former (not shown) for converting the reflected wave received from the ultrasonic probe 12 into an electrical signal (hereinafter referred to as a 'reception signal').

The above-described transmission beam former and reception beam former are generally implemented using two types of beam former circuits, that is, digital and analog beam former circuits.

Those two types of beam formers may occasionally share common hardware blocks, and both require a plurality of suitable channels (typically, 32 or more channels).

The beam focusing unit 16 focuses the reception signal and transfers the focused reception signal to the image processing unit 18.

The image processing unit 18 generates and processes ultrasonic image data (hereinafter referred to as 'primary ultrasonic image data') on the basis of the reception signal received through the beam focusing unit 16.

Figure 2:
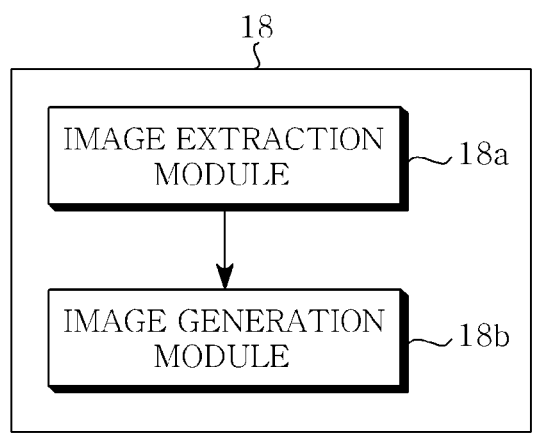
FIG. 2 is a detailed block diagram showing the image processing unit of FIG. 1.

FIG. 2 is a detailed block diagram showing the image processing unit of FIG. 1.

Referring to FIG. 2, the image processing unit 18 includes an image extraction module 18a and an image generation module 18b.

The image extraction module 18a divides the reception signal with a predetermined sound velocity focused by the beam focusing unit 16 into a plurality of (for example, n) signals, and extracts respective image signals from the n signals.

In the present invention, for convenience of description, it is assumed that the sound velocity of the ultrasonic wave emitted from the ultrasonic probe 12 ranges from 1400 m/s to 1590 m/s and that the image extraction module 18a divides the reception signal with such a sound velocity by 10 m/s and extracts ultrasonic image signals of 20 frames from 20 reception signals.

The image generation module 18b generates primary ultrasonic image data of 20 frames on the basis of the 20 image signals extracted by the image extraction module 18b.

The primary ultrasonic image data of 20 frames generated in this way is stored in the storage unit 22 by the memory controller 30a of the control unit 30 in the form of a look-up table (LUT) 22a.

Further, when an optimal frame is selected from among the plurality of frames by the sound velocity determination unit 20 which will be described later, the image processing unit 18 generates secondary ultrasonic image data by extracting a contour from the primary ultrasonic image data of the optimal frame using morphological contour extraction, and processes the secondary ultrasonic image data.

The sound velocity determination unit 20 estimates the actual sound velocity of the reflected wave, which is reflected from the internal tissue of the human body, in real time by using the plurality of pieces of primary ultrasonic image data, and then determines the estimated actual sound velocity to be the optimal sound velocity.

For this operation, the sound velocity determination unit 20 is operated in two operating modes.

The first operating mode is an optimal block selection mode in which one of the pieces of primary ultrasonic image data of the plurality of frames is divided into a plurality of blocks and pieces of primary ultrasonic image data of respective blocks are compared and analyzed, and thus an optimal block is selected.

The second operating mode is an optimal frame selection mode in which blocks at the locations of the remaining frames, corresponding to the location of the optimal block selected in the first operating mode, are applied to the remaining frames and are determined to be optimal blocks of the corresponding frames and in which pieces of primary ultrasonic image data of respective optimal blocks of the frames are compared and analyzed, and thus an optimal frame is ultimately selected.

The sound velocity determination unit 20 estimates the sound velocity of the optimal frame, ultimately selected in the first and second operating modes, to be actual sound velocity, and determines the estimated actual sound velocity to be the optimal sound velocity.

Figure 3:
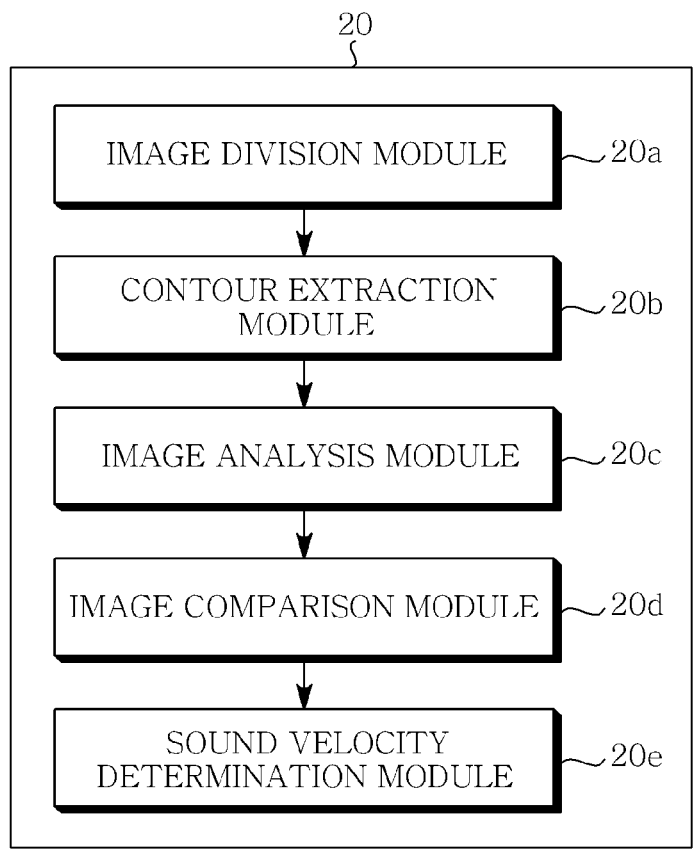
FIG. 3 is a detailed block diagram showing the sound velocity determination unit of FIG. 1.

FIG. 3 is a detailed block diagram showing the sound velocity determination unit of FIG. 1.

Referring to FIG. 3, the sound velocity determination unit 20 includes an image division module 20a, a contour extraction module 20b, an image analysis module 20c, an image comparison module 20d and a sound velocity determination module 20e.

First, an operation in the first operating mode will be described in detail.

The image division module 20a reads pieces of primary ultrasonic image data of 20 frames stored in the storage unit 22, and divides the primary ultrasonic image data of each of first to 20-th frames by applying the same division matrix (for example, an N×M matrix) to the individual frames.

Figure 4:
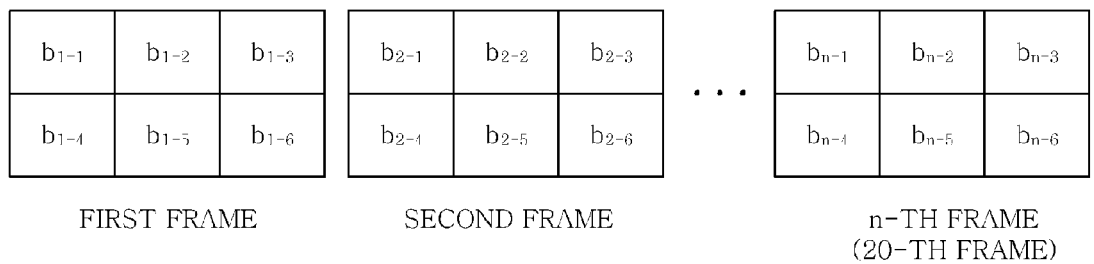
FIG. 4 is a diagram showing an example of the division of primary ultrasonic image data performed by the image division module of FIG. 3.
Figure 5:
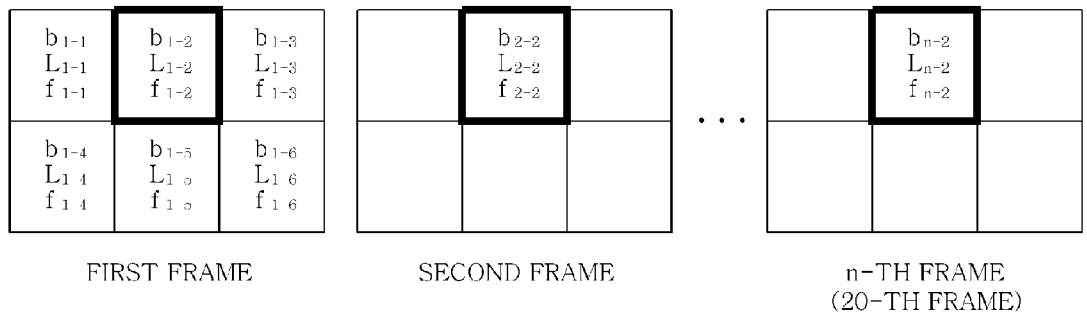
FIG. 5 is a diagram showing an example in which an optimal block is selected from the first frame of FIG. 4 and is applied to a plurality of frames.

FIG. 4 is a diagram showing an example of the division of primary ultrasonic image data performed by the image division module of FIG. 3, and FIG. 5 is a diagram showing an example in which an optimal block is selected from the first frame of FIG. 4 and is applied to a plurality of frames.

For convenience of description, the image division module 20a according to the present embodiment is assumed to divide the primary ultrasonic image data of each of first to 20-th frames into 3×2 blocks.

Then, as shown in FIG. 4, the primary ultrasonic image data of each of the first to 20-th frames is divided into six blocks by the image division module 20a (for example, the first frame is divided into blocks $b_{1-1}, b_{1-2}, b_{1-3}, \ldots, b_{1-6}$), and the location coordinates of individual blocks of each frame are recorded and stored in the look-up table (LUT) 22a of the storage unit 22, together with each frame number.

The contour extraction module 20b generates block-based ultrasonic image data (hereinafter referred to as 'block image data') which is reconstructed by extracting contours from the primary ultrasonic image data of the blocks of the first frame, divided into the six blocks by the image division module 20a, in such a way as to apply morphological contour extraction to each block. The contour extraction module 20b records and stores six pieces of block image data corresponding to the six blocks in the LUT 22a of the storage unit 22.

The image analysis module 20c analyzes the block image data of each block of the first frame.

As shown in FIG. 5, the image analysis module 20c reads block image data of each of six blocks of the first frame stored in the storage unit 22, and calculates the luminance value and high-frequency (HF) component value of the block image data of each block, and thus digitizes the block image data of each block.

Further, the entire luminance value of the first frame is calculated by obtaining the mean of the luminance values of the six blocks. The entire luminance value is used to select a structuring function to be applied according to the entire illuminance value of a frame to which morphological contour extraction, which will be described later, is to be applied when a contour is extracted using morphological contour extraction.

That is, when a frame to which morphological contour extraction is to be applied is excessively bright or dark, it is difficult to extract contours, so that a kind of weight matrix (a structuring function) is set for the frame to which morphological contour extraction is to be applied before the morphological contour extraction is applied, thus adjusting the entire luminance of the frame.

The luminance values and HF component values of six blocks of the first frame and the entire luminance value of the first frame, which have been digitized in this way, are recorded and stored in the LUT 22a of the storage unit 22.

The image comparison module 20d individually compares the luminance values and HF component values of six pieces of block image data of the first frame, which have been digitized, with each other, and transmits optimal block image data of the first frame, corresponding to the maximum luminance value and the maximum HF component value, to the sound velocity determination module 20e.

The sound velocity determination module 20e selects a block corresponding to the optimal block image data of the first frame, received from the image comparison module 20d, as the optimal block of the first frame, and records and stores the location coordinates of the optimal block of the first frame in the LUT 22a of the storage unit 22.

As described above, the optimal block of the first frame is selected in the first operating mode.

Next, an operation in the second operating mode will be described in detail.

The contour extraction module 20b determines blocks at the locations of the remaining frames, corresponding to the location indicated by the location coordinates of the optimal block of the first frame selected in the first operating mode, to be the optimal blocks of the corresponding frames, that is, second to 20-th frames.

Pieces of optimal block image data of the second to 20-th frames, reconstructed by extracting a contour from each of the optimal blocks of the second to 20-th frames using morphological contour extraction, are generated and are recorded and stored in the LUT 22a of the storage unit 22.

The image analysis module 20c analyzes the pieces of optimal block image data of the first to 20-th frames.

In detail, the image analysis module 20c reads optimal block image data of the respective optimal blocks of the first to 20-th frames, stored in the storage unit 22, calculates the luminance values and HF component values of the individual pieces of optimal block image data, and then digitizes the pieces of optimal block image data.

The luminance values and HF component values of the respective pieces of optimal block image data of the first to 20-th frames, which have been digitized in this way, are recorded and stored in the LUT 22a of the storage unit 22.

The image comparison module 20d individually compares the luminance values and HF component values of the respective pieces of optimal block image data of the first to 20-th frames, which have been digitized, with each other, and transmits the optimal block image data of a frame, corresponding to the maximum luminance value and the maximum HF component value, to the sound velocity determination module 20e.

The sound velocity determination module 20e selects a frame corresponding to the optimal block image data, received from the image comparison module 20d, as an optimal frame, estimates the sound velocity of the optimal block image data of the optimal frame to be the actual sound velocity of the reflected wave, and determines the estimated actual sound velocity to be the optimal sound velocity.

As described above, the optimal frame having optimal block image data is selected in the second operating mode, and the optimal sound velocity is determined based on the optimal frame.

In order to describe in detail a method of reconstructing an image according to morphological contour extraction used in the first and second operating modes of the contour extraction module 20b, the following equations for morphological operations are to be used for reference.

$$(f \ominus b)(x) = \min_{z-x \in D_f,\ z \in D_b} \{f(z-x) - b(z)\} \quad (1)$$

$$(f \oplus b)(x) = \min_{z-x \in D_f,\ z \in D_b} \{f(z-x) + b(z)\} \quad (2)$$

$$(f \cdot b) = (f \ominus b) \oplus b \quad (3)$$

$$(f \cdot b) = (f \oplus b) \ominus b \quad (4)$$

$$E_d(f) = (f \oplus b) - f \quad (5)$$

$$E_e(f) = f - (f \ominus b) \quad (6)$$

$$E_o(f) = f - (f \cdot b) \quad (7)$$

$$E_c(f) = (f \cdot b) - f \quad (8)$$

$$E_f(f) = (((f \cdot b) \cdot b) \cdot b) - (((f \cdot b) \cdot b) \cdot b) \oplus b \quad (9)$$

$$E_f(f) = (((f \cdot b) \cdot b) \cdot b) \ominus b - (((f \cdot b) \cdot b) \cdot b) \quad (10)$$

$$F(x) = \{f(z-x) \times k(z)\} \quad (11)$$

$$\text{Cal\_Lum} = \{f(z-x-m)/(\text{pix\_cnt\_t}/m)\} \quad (12)$$

$$\text{Block\_sum\_n} = \{f(z-x-m)/(\text{pix\_cnt\_bn}/m)\} \quad (13)$$

The above equations represent morphological operation methods for a grayscale image in linear functions.

In this case, f denotes a grayscale input image, and b denotes a grayscale structuring element for adjusting the results of a morphological operation.

Further, f(z−x) denotes the grayscale value of a pixel, and b(z) denotes a structuring function.

In the case of the structuring function b(z), maximum/minimum filters can be implemented using structuring functions having specific forms. For example, an erosion operation functions as a minimum filter, and a dilation operation functions as a maximum filter.

Meanwhile, $E_d(f)$, $E_e(f)$, $E_o(f)$, and $E_c(f)$ represent image values, obtained by respectively performing dilation, erosion, opening and closing operations on each image, in functions.

In detail, Equation (1) denotes an erosion operation among morphological operations, and this exhibits the effect of eroding an object region in an image and is consequently used to reduce the size of an object.

Equation (2) denotes a dilation operation among morphological operations, and this exhibits the effect of dilating an object region in such a way as to fill small holes and is consequently used to dilate the size of an object.

Equation (3) denotes an opening operation among morphological operations, and this exhibits the effect of smoothing the contour of an object and eliminating thin protrusions. Therefore, the opening operation is occasionally useful to eliminate noise or separate an object.

Equation (4) denotes a closing operation among morphological operations, and this exhibits the effect of filling thin valleys contrary to the above-described opening operation. Therefore, the closing operation is useful to combine objects.

As described above, the erosion and opening operations can sharpen images, and the dilation and closing operations can dilate images. Therefore, effective contours can be formed by suitably using the properties of such morphological operations.

When Equations (5) and (6) are applied to ultrasonic image data, the contour of an object can be effectively extracted, but noise may occur. When Equations (7) and (8) are applied to ultrasonic image data, the contour of an object is ineffectively extracted, but noise can be eliminated.

The contour of ultrasonic image data can be effectively extracted by suitably using the above-described erosion, dilation, closing and opening operations.

In order to obtain optimal ultrasonic image data based on the effective contour extraction of ultrasonic image data, in an embodiment of the present invention, the optimal ultrasonic image data computed by suitably using Equations (1) to (8) is represented in the functions given in Equations (9) and (10).

Morphological contour extraction for optimal ultrasonic image data based on Equation (9) will be described below. First, opening (elimination of thin protrusions)→closing (filling of thin valleys)→opening (elimination of noise) operations among morphological operations are sequentially performed on the ultrasonic image data, so that noise-free first morphological image data is generated and then stored.

Simultaneously with the generation of the first morphological image data, a dilation operation among morphological operations is performed on the first morphological image data, so that second morphological image data is generated and then stored.

Next, when a differential image is obtained by subtracting the second morphological image data from the first morphological image data after the first and second morphological image data has been read, the contour of the ultrasonic image data of the internal tissue of the examinee can be effectively extracted.

Contrary to Equation (9), morphological contour extraction for optimal ultrasonic image data based on Equation (10) will be described below. First, closing (filling of thin valleys)→opening (elimination of noise)→closing (filling of thin valleys) operations among morphological operations are sequentially performed on the ultrasonic image data, so that noise-free first morphological image data is generated and then stored.

Simultaneously with the generation of the first morphological image data, an erosion operation among the morphological operations is performed on the first morphological image data, so that second morphological image data is generated and then stored.

Next, when a differential image is obtained by subtracting the first morphological image data from the second morphological image data after the first and second morphological image data has been read, the contour of the ultrasonic image data of the internal tissue of the examinee can be effectively extracted.

Meanwhile, Equation (11) represents an image value, obtained by multiplying a weight matrix by a grayscale image and adjusting the entire luminance value and the entire HF component value, by a function, where k(z) is a weight matrix.

Equation (12) is an equation for computing the entire luminance value of the grayscale image, and Equation (13) is an equation for computing the HF components of respective blocks of the grayscale image divided into n blocks. In this case, pix_cnt_t denotes the total pixel value of the entire grayscale image, pix_cnt_bn denotes the pixel value of each block, and m denotes a constant indicating the width of a pixel.

Such morphological contour extraction is equally applied to the first and second to operating modes of the contour extraction module 20b.

Referring back to FIG. 1, the storage unit 22 stores various types of data generated by the image processing unit 18 and the sound velocity determination unit 20, for example, the plurality of pieces of primary ultrasonic image data, the luminance values and HF component values of the primary ultrasonic image data, the plurality of pieces of block image data, the luminance values and HF component values of the block image data, a weight corresponding to the mean luminance value, and a morphology matrix corresponding thereto. Further, the storage unit 22 may store the above data configured in the form of the LUT 22a.

The data output unit 24 outputs secondary ultrasonic image data which is generated in the image processing unit 18 by applying morphological contour extraction to the primary ultrasonic image data of the optimal frame.

Since the data output unit 24 outputs secondary ultrasonic image data with the optimal sound velocity, which is determined in the sound velocity determination unit 20 by estimating the actual sound velocity corresponding to the internal tissue of the human body in real time, ultrasonic images having excellent quality can be monitored in real time.

As the data output unit 24, a monitor is used.

The interface 26 transmits a control signal to the ultrasonic transmission unit 28 under the control of the control unit 30.

There are two types of control signals transmitted from the control unit 30 to the ultrasonic transmission unit 28 through the interface 26.

One is a control signal which enables the ultrasonic transmission unit 28 to generate a transmission signal with a sound velocity preset by the control unit 30, and the other is a control signal which enables the ultrasonic transmission unit 28 to generate a transmission signal with an optimal sound velocity determined by the sound velocity determination unit 20.

The control unit 30 controls the entire operation of the ultrasonic diagnostic apparatus 1 according to the embodiment of the present invention.

Control performed by the control unit 30 will be described in detail with reference to FIGS. 6 and 7.

Figure 6:
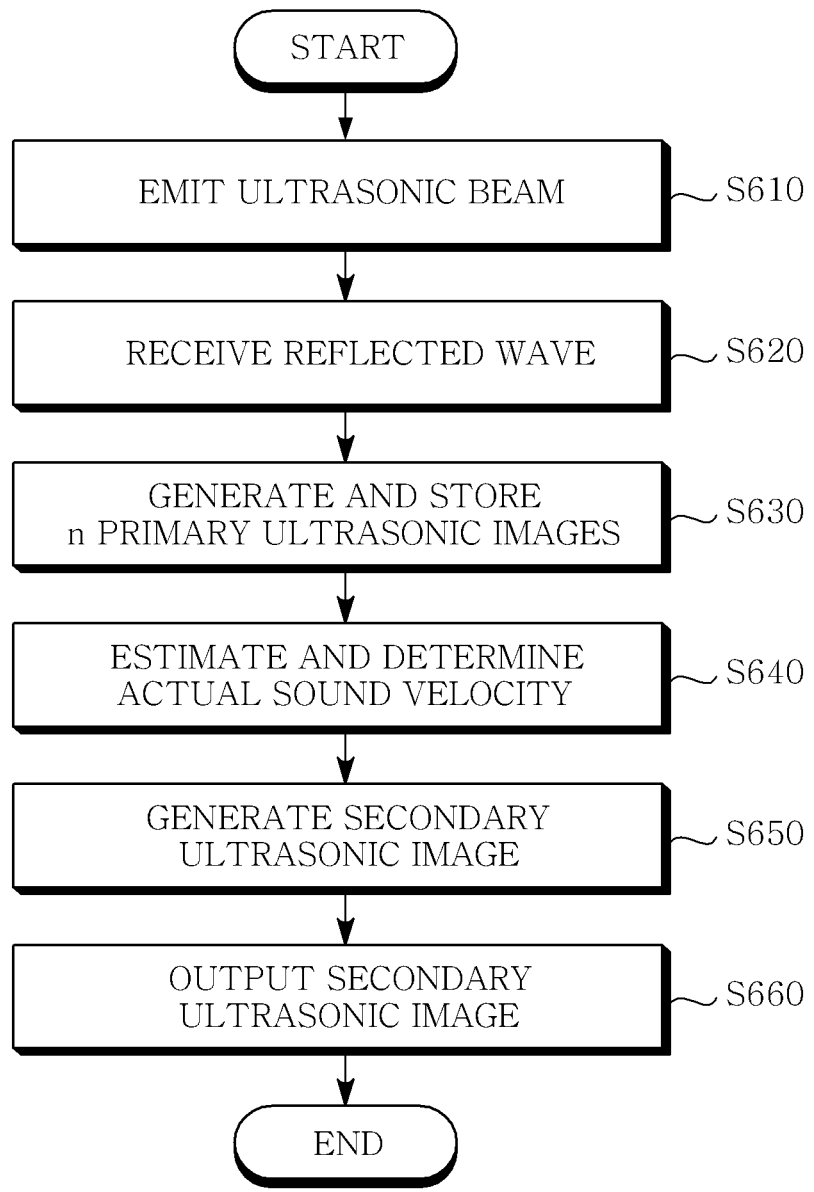
FIG. 6 is a flowchart showing an ultrasonic image processing method performed by the ultrasonic diagnostic apparatus according to an embodiment of the present invention.

FIG. 6 is a flowchart showing an ultrasonic image processing method performed by the ultrasonic diagnostic apparatus according to an embodiment of the present invention.

Referring to FIG. 6, the control unit 30 of the ultrasonic diagnostic apparatus 1 according to the embodiment of the present invention generates a transmission signal in response to a control signal, converts the transmission signal into an ultrasonic beam, and emits the ultrasonic beam to a target (S610).

Next, a reflected wave, which is returned from the target after the ultrasonic beam has been reflected from the target, is received (S620).

The reflected wave received in this way is converted into a plurality of reception signals in such a way as to divide the reflective wave with a sound velocity by a predetermined unit (for example, 10 m/s) and extract the plurality of reception signals, and pieces of primary ultrasonic image data of a plurality of frames are generated from the reception signals and are then stored (S630).

Next, after an optimal block is selected from the primary ultrasonic image data of any one of the plurality of frames, blocks at the locations of the remaining frames, corresponding to the location of the optimal block, are determined to be the optimal blocks of the corresponding frames, so that an optimal frame is selected, and the sound velocity of the optimal frame is estimated to be the actual sound velocity of the reflected wave and is determined to be the optimal sound velocity (S640).

Thereafter, the contour of the primary ultrasonic image data of the optimal frame is extracted, and thus secondary ultrasonic image data is generated (S650). A secondary ultrasonic image which has been ultimately generated is output to the data output unit (S660).

Figure 7:
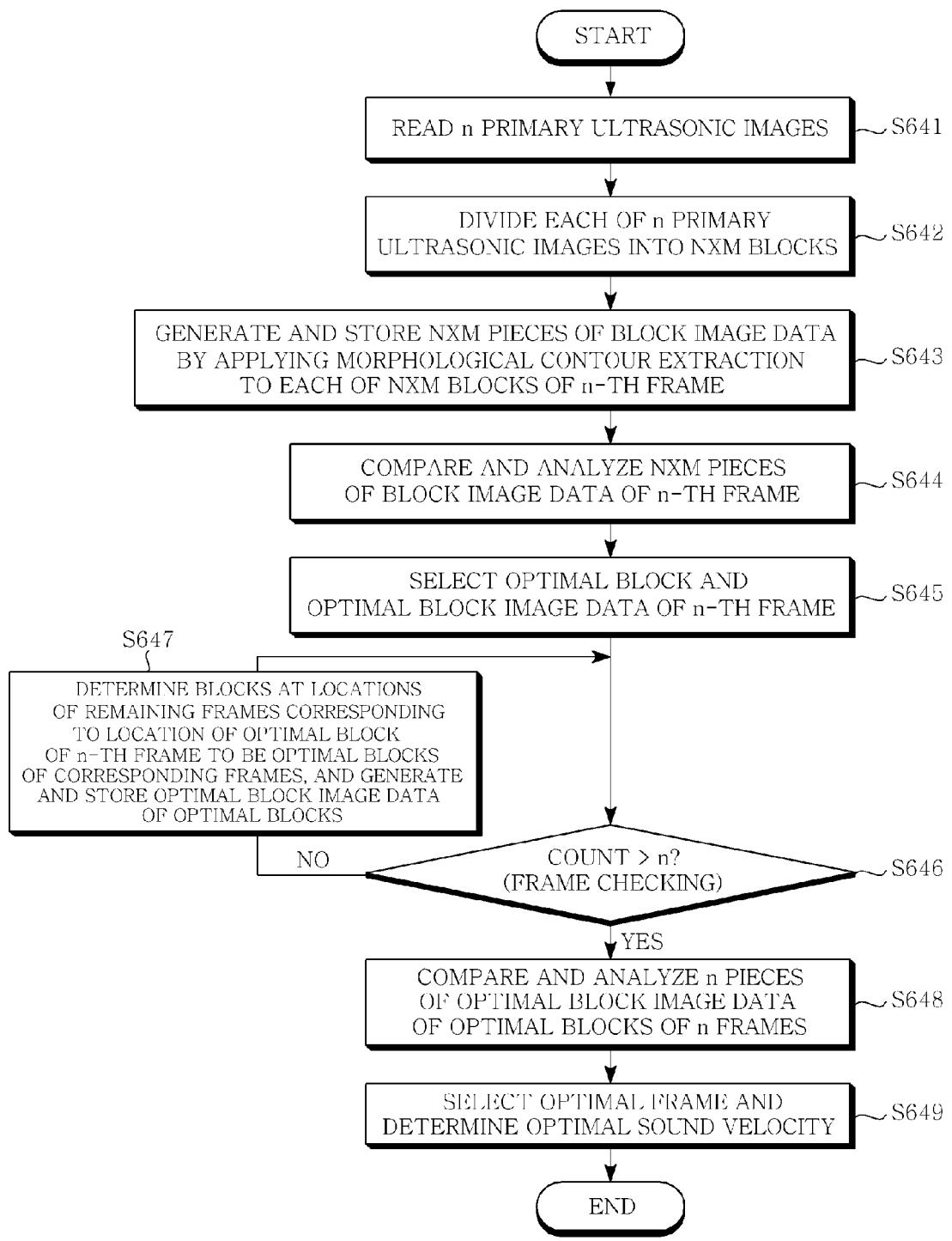
FIG. 7 is a detailed flowchart showing the sound velocity determination of FIG. 6.

FIG. 7 is a detailed flowchart showing the sound velocity estimation and determination operation (S640) of FIG. 6.

Referring to FIG. 7, in order to determine a sound velocity according to an embodiment of the present invention, the control unit 30 controls the sound velocity determination unit 20 so that it is operated in the first operating mode (S641 to S645) and the second operating mode (S646 to S649).

In detail, the control unit 30 reads primary ultrasonic image data of n frames from the storage unit 22 (S641), and divides the primary ultrasonic image data of each of the n frames into a plurality of blocks (for example, N×M blocks) (S642).

Next, morphological contour extraction is applied to each of the N×M blocks of an n-th frame among n pieces of primary ultrasonic image data, so that N×M pieces of block image data are generated and stored (S643).

Thereafter, the luminance values and HF component values of the N×M pieces of block image data of the n-th frame are individually compared and analyzed (S644). Thereafter, a block having the maximum luminance value and the maximum HF component value is selected as an optimal block, and the block image data of the optimal block is selected as the optimal block image data of the n-th frame (S645).

Next, whether all pieces of optimal block image data of respective optimal blocks of the n frames have been generated is determined (S646). In detail, in order to determine blocks at the locations of the remaining frames corresponding to the location of the optimal block of the n-th frame to be the optimal blocks of the corresponding frames, frame checking is performed by determining whether a frame number is greater than n.

At S646, if the frame number is equal to or less than n, blocks at the locations of the remaining frames corresponding to the location of the optimal block of the n-th frame are determined to be the optimal blocks of corresponding frames, and pieces of optimal block image data of the optimal blocks are generated and stored (S647).

At S646, if the frame number is greater than n, the luminance values and HF component values of the n pieces of optimal block image data of the respective optimal blocks of the n frames, generated at S645, are individually compared and analyzed (S648). Thereafter, a frame having the maximum luminance value and the maximum HF component value is selected as an optimal frame, and the sound velocity of the optimal frame is estimated to be the actual sound velocity of the reflected wave and is determined to be the optimal sound velocity (S649).

As described above, an ultrasonic diagnostic apparatus and ultrasonic image processing method according to embodiments of the present invention not only can provide ultrasonic image data having better quality by estimating the actual sound velocity of a reflected wave which is generated when an ultrasonic beam emitted into a human body is reflected from the internal tissue of the human body, but also can shorten the time required to process ultrasonic images by selecting and comparing only part of ultrasonic images rather than all of them at the time of estimating a sound velocity.

According to the present invention, the ultrasonic diagnostic apparatus is advantageous in that a sound velocity is estimated in real time and applied depending on various types of media of the internal tissue of a human body, so that the distortion of ultrasonic images generated by a reflected wave which is returned from the internal tissue after an ultrasonic beam has been reflected therefrom can be reduced, and thus the image quality of ultrasonic images can be improved.

Further, the present invention is advantageous in that only part of ultrasonic images rather than all of them are compared and analyzed, so that the time required for the estimation of a sound velocity can be reduced, and thus the speed of the ultrasonic diagnostic apparatus can be improved.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An ultrasonic image processing method, comprising:
   (A) generating a transmission signal in response to a control signal, converting the transmission signal into an ultrasonic beam, and emitting the ultrasonic beam to a target;
   (B) receiving a reflected wave which is returned from the target after the ultrasonic beam has been reflected from the target, dividing the reflected wave into a plurality of reception signals, extracting the reception signals, generating primary ultrasonic image data of a plurality of frames from the reception signals, and storing the primary ultrasonic image data of the frames;
   (C) dividing primary ultrasonic image data of any one frame among primary ultrasonic image data of the plurality of frames into a plurality of blocks, extracting the luminance value and the high-frequency component values of block image data from individual blocks, selecting a block having maximum luminance value and maximum high-frequency component values as an optimal block by comparing the luminance value and the high frequency component values of block image data from individual blocks, determining blocks at locations of remaining frames, corresponding to a location of the optimal block, to be optimal blocks of corresponding frames, selecting an optimal frame, and determining a sound velocity of the optimal frame to be an actual sound velocity of the reflected wave; and
   (D) generating secondary ultrasonic image data by extracting a contour from primary ultrasonic image data of the optimal frame, and then outputting the secondary ultrasonic image data.

2. The ultrasonic image processing method as set forth in claim 1, wherein (C) comprises:
   (C-1) reading the primary ultrasonic image data of the plurality of frames and dividing primary ultrasonic image data of each frame into a plurality of blocks;
   (C-2) generating a plurality of pieces of block image data by extracting contours from individual blocks of the primary ultrasonic image data of any one frame among the primary ultrasonic image data of the frames, and selecting an optimal block from the plurality of pieces of block image data;
   (C-3) determining blocks at locations of remaining frames, corresponding to the location of the optimal block, to be the optimal blocks of the corresponding frames, generating a plurality of pieces of optimal block image data by extracting contours from primary ultrasonic image data of the respective optimal blocks of the frames, and selecting the optimal frame from the plurality of pieces of optimal block image data; and
   (C-4) determining a sound velocity of the optimal frame to be an optimal sound velocity of the reflected wave.

3. The ultrasonic image processing method as set forth in claim 2, wherein (C-2) comprises:
   extracting the contours by performing a morphological operation on the primary ultrasonic image data of the plurality of blocks, thus generating the plurality of pieces of block image data;
   calculating luminance values and High-Frequency (HF) component values of the plurality of pieces of block image data; and
   individually comparing the luminance values and the HF component values, and selecting a block having a maximum luminance value and a maximum HF component value as the optimal block.

4. The ultrasonic image processing method as set forth in claim 2, wherein (C-3) comprises:
   determining the blocks at the locations of the remaining frames, corresponding to the location of the optimal block, to be the optimal blocks of the corresponding frames, and extracting the contours from the primary ultrasonic image data of the respective optimal blocks of the frames by performing the morphological operation on the primary ultrasonic image data, thus generating the plurality of pieces of optimal block image data;
   determining whether generation of all of optimal block image data of the respective optimal blocks of the frames has been completed;
   calculating luminance values and HF component values of the plurality of pieces of optimal block image data; and
   selecting a frame having a maximum luminance value and a maximum HF component value as the optimal frame by individually comparing the luminance values and the HF component values from the plurality of pieces of optimal block image data.

* * * * *